United States Patent [19]

Hellstrom

[11] Patent Number: 5,099,125
[45] Date of Patent: Mar. 24, 1992

[54] SHEET MATERIAL SENSOR COMPENSATION

[75] Inventor: Ake A. Hellstrom, Columbus, Ohio

[73] Assignee: ABB Process Automation Inc., Columbus, Ohio

[21] Appl. No.: 655,620

[22] Filed: Feb. 15, 1991

[51] Int. Cl.$^5$ .......................... G01B 5/04; G01B 5/06; G01N 23/00
[52] U.S. Cl. ................. 250/358.1; 250/308; 250/359.1; 73/159
[58] Field of Search ............... 250/308, 358.1, 359.1; 73/159

[56] References Cited

U.S. PATENT DOCUMENTS 4,678,915  7/1989  Dahlquist et al. ............... 250/358.1
5,010,766  4/1991  Tuppo ........................... 73/159
5,021,666  6/1991  Reber ............................ 250/359.1

*Primary Examiner*—Constantine Hannaher
*Assistant Examiner*—Edward J. Glick
*Attorney, Agent, or Firm*—Paul J. Lerner

[57] ABSTRACT

A device for measuring the gap between the radiation source and the radiation sensor of a basis weight gauge. A caliper sensor measures the thickness of a sheet of material as it passes through the gap, while the caliper contact shoe rides on the sheet and urges it against a first side of the gap. A linear variable differential transformer measures the distance between a reference point on the contact shoe and the opposed side of the gap. The gap dimension is the sum of the sheet thickness, the distance between the caliper reference point and the second side of the gap, and a readily measurable constant.

3 Claims, 2 Drawing Sheets

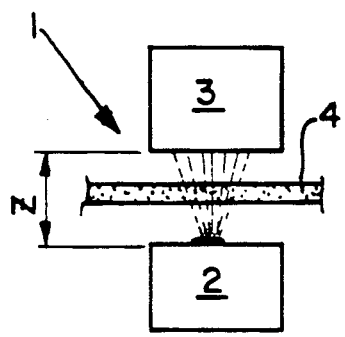
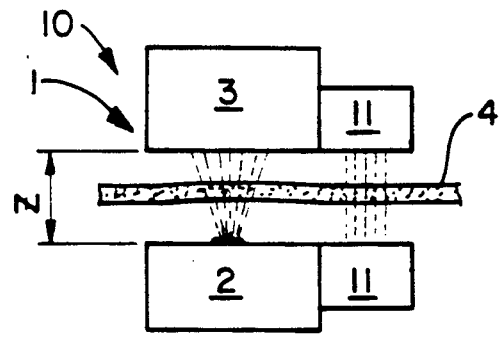
Fig. 1 (Prior Art)   Fig. 3 (Prior Art)
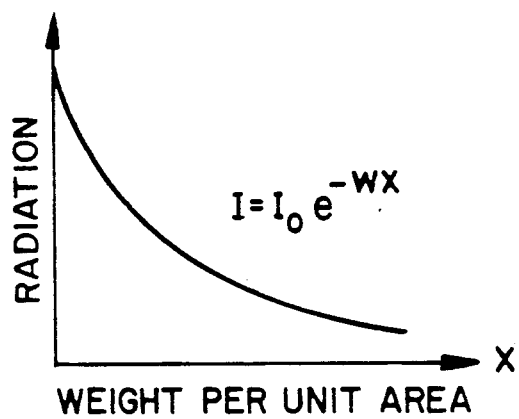
$I = I_0 e^{-wx}$
Fig. 1A
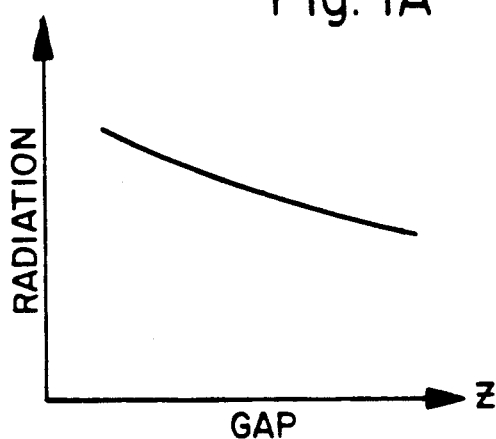
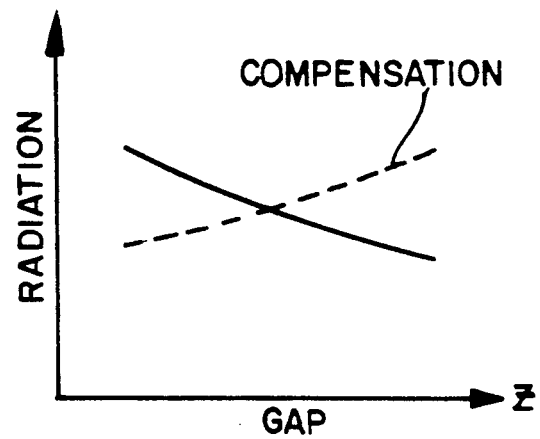
Fig. 2   Fig. 4

SHEET MATERIAL SENSOR COMPENSATION

BACKGROUND AND SUMMARY OF THE INVENTION

The present invention relates to a radiation-type apparatus for measuring the basis weight of a sheet of material and, more particularly, to a means for accurately measuring the gap between the radiation source and the radiation sensor and compensating for variations therein.

Systems for measuring certain parameters of a moving sheet of material are well known in the art. For example, a system for measuring basis weight employs a gauge disposed with one part thereof on either side of the moving sheet, the gauge being mounted in a frame and adapted to travel transversely of the sheet. A radiation source is located in the lower gauge portion and a radiation detector is located in the upper gauge portion to receive radiation from the source. The amount of radiation received by the sensor is related to the basis weight of the sheet, and thus the gauging system monitors the basis weight as the sheet travels between the two gauge portions.

Parameters other than the basis weight of the sheet can be measured by systems similar to the one above-described. For example, the moisture content of a sheet of material may be measured by a device including a source of infrared radiation located in a gauging head member disposed on one side of the sheet and a detector or receiver of the radiation located in a head member disposed on the other side of the sheet. Opacity of the sheet can also be measured by a similar system.

In gauging systems of this type, the accuracy of the parameter measurement may be severely affected by variation in the distance or gap between the two gauging head parts. While means are known to correct the measured parameter values to compensate for such variations, such means are dependent upon accurate distance or gap measurement. One such method, described in U.S. Pat. No. 4,678,915, involves a magnetic measurement of the gap utilizing a transducer system mounted with the other sensors on the gauging head. Such a system, however, has significant limitations in that temperature effects and magnetic sensor accuracy are both proportional to the distance being measured. Thus, when measuring the distance across a relatively large gap, it is difficult to precisely measure small variations therein. The effects of lateral displacements on measurement accuracy also become more pronounced as gap distance increases.

It is, therefore, a primary object of the present invention to provide an improved basis weight measuring device, of the type comprising a radiation source and a radiation sensor spaced therefrom across a gap, including means for precisely measuring variations in the gap between the source and the sensor and for adjusting the sensor output signal in response thereto.

It is a further object to provide an improved device for precisely measuring the gap between the parts of a gauging head of a sheet-making machine and, more particularly, to provide such a device which minimizes or eliminates the effects of temperature variations and lateral displacements.

These objects are achieved, in general, by a basis weight measuring device of the aforementioned type wherein caliper means are provided to measure the thickness of the sheet, a portion of the caliper riding on the sheet and urging it against a first side of the gap, and second measurement means are provided to measure the distance between a reference point on the sheet-riding portion of the caliper means and the second side of the gap. The gap dimension is thus the sum of the thickness of the sheet, the distance between the base of the sheet-riding portion of the caliper means and the reference point thereon, and the distance between the caliper reference point and the second side of the gap. The first of these components may be precisely measured by conventional thickness gauges, such as the AccuRay Caliper sensor sold by ABB Process Automation Inc. The second component is a predetermined constant, defined by the sensor geometry and system dimensions. The third component may be measured by a conventional linear variable differential transformer (L.V.D.T.) such as the Model 100HR sold by Schaevitz Corp. Because this third component has relatively small variability, typically ⅛ inch or less, the aforementioned measurement limitations are avoided and great precision is achieved.

BRIEF DESCRIPTION OF THE DRAWINGS

FIG. 1 is a simplified view of a conventional basis weight gauge.

FIG. 1A is a representative performance graph of the weight gauge of FIG. 1.

FIG. 2 is a representative graph showing the relation between radiation source-to-sensor separation and indicated basis weight.

FIG. 3 is a simplified view of a conventional basis weight gauge with a compensation sensor.

FIG. 4 is a representative performance graph of the weight gauge of FIG. 3.

DETAILED DESCRIPTION OF THE PREFERRED EMBODIMENT

Figure 5:
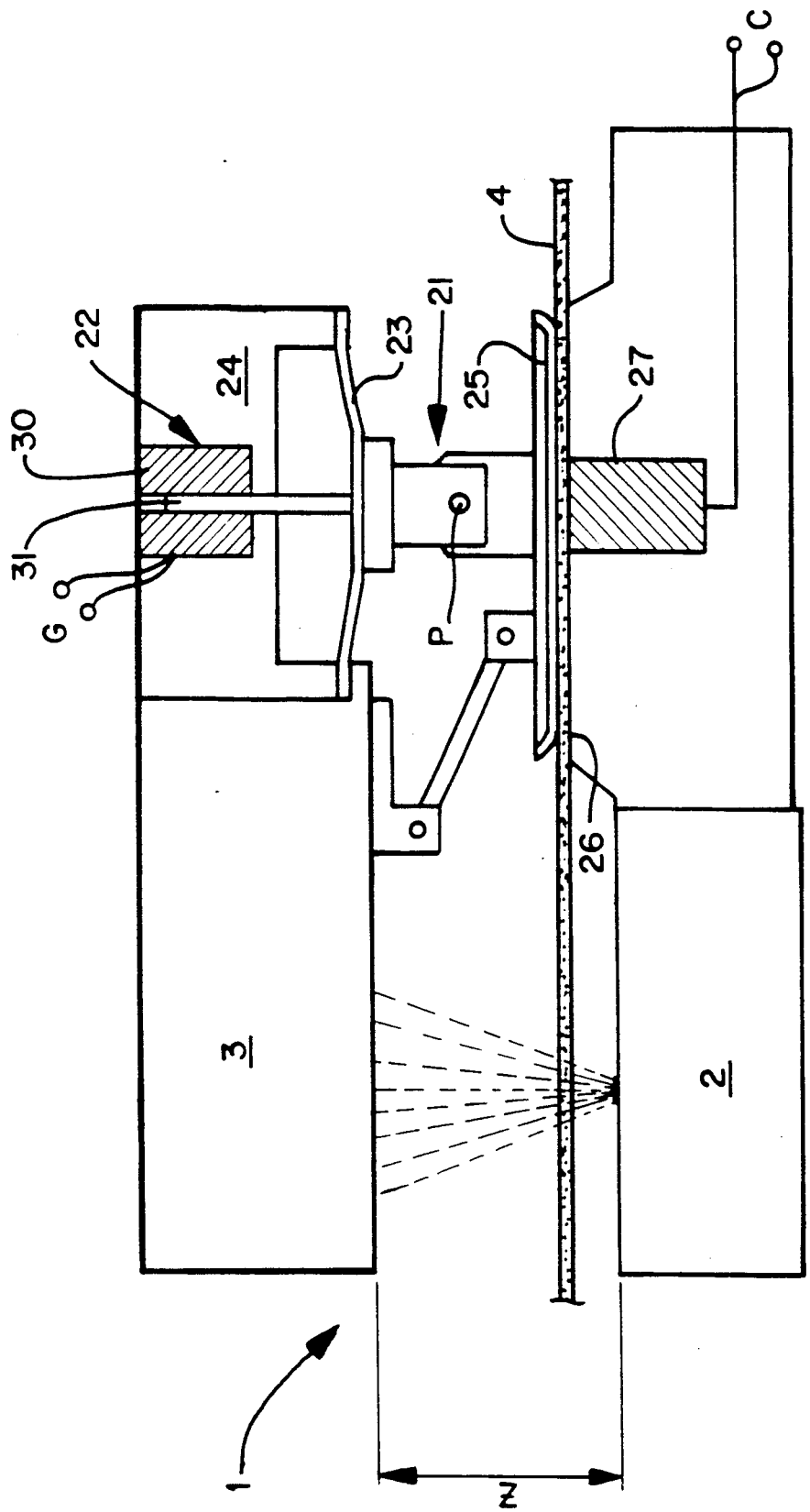
FIG. 5 is a simplified view of a basis weight measurement device in accord with the present invention.

Turning now to the drawing, there is seen generally in FIG. 1, a conventional basis weight gauge 1 comprising a radiation source 2 and a radiation sensor 3 disposed on opposite sides of a gap Z through which passes a sheet of material 4 to be measured. Radiation source 2 and sensor 3 are mounted on a frame (not shown) which is adapted to travel transversely of sheet 4, along cross-machine beams (not shown).

As illustrated in the representative graph of FIG. 1A, the amount of radiation received by sensor 3 is related to the basis weight of sheet 4 by the formula $I = I_o e^{-wx}$ where $I_o$ is the intensity of radiation reaching the sensor when there is no sheet of material in the gap; w is the mass absorption coefficient of the material; x is the weight per unit area of the sheet of material; and I is the intensity of received radiation when the sheet material is in the gap. Use of this formula requires that the radiation source and sensor be spaced a constant distance apart and that the system be calibrated accordingly. In practice, however, the distance between radiation source 2 and radiation sensor 3 is not constant. Therefore, the level of radiation received by sensor 3 is dependent on the source-to-detector separation "Z" as well as the process weight per unit area. This relation is graphed in FIG. 2. On a traversing frame, the separation between the beams is not precisely the same throughout their entire length. Consequently, as the scanning heads move along the beams, the separation between the radiation source 2 and sensor 3 will change. Also, the beams and the frame can change temperature during operation. For example, in the paper making process the paper is often quite hot, which causes the basis weight gauge to be hot. However, if the paper breaks and the process is shut down for some time, the gauge can become relatively cool. When the process resumes, the gauge begins to heat due to the heat of the paper. Thus, the beams can deform slightly, causing the separation or gap Z between radiation source 2 and sensor 3 to vary.

In FIG. 3 there is shown generally a basis weight measuring system 10 including gauge 1 and a distance compensation means as taught in U.S. Pat. No. 4,678,915. A magnetic inductance distance measuring device 11, mounted with radiation source 2 and sensor 3, provides a continuous measurement of gap Z, which measurement is processed by a computer (not shown) to provide a distance compensation input to radiation sensor 3. For the reasons previously noted, however, such compensation has not proven entirely satisfactory on large measurement gaps Z.

There is shown, in FIG. 5, a basis weight measurement device in accord with the present invention, including a conventional basis weight gauge 1, a conventional caliper sensor 21 of the type aforementioned and a conventional linear variable differential transformer 22, also of the type aforementioned.

Caliper 21 includes a diaphragm 23 on the upper frame portion directing a contact shoe 25 against sheet 4 which is thus urged against a caliper contact surface 26 on the lower frame portion. Diaphragm 23 pneumatically communicates with pneumatic chamber 24 affixed to radiation sensor 3. A caliper sensing coil 27, disposed beneath contact surface 26, co-operates with contact shoe 25, in a known manner, to precisely measure the thickness of sheet 4.

Linear variable differential transformer 22 includes a position transducer coil 30 disposed within pneumatic chamber 24. Coil 30 co-operates with a core 31 connected to contact shoe 25, in a known manner, to precisely measure the distance between a reference point P on contact shoe 25 and the opposing side of gap Z. Thus, the measure of gap Z is the sum of the thickness of sheet 4, measured by caliper sensor 21 (output C), the distance between reference point P of contact shoe 25 and the opposed side of gap Z (output G), and a constant, determined by the geometry of the device, which may be readily measured.

Reference point P is chosen so as to minimize the variability in distance between itself and the opposing side of gap Z. Preferably, there is a direct connection and a very short distance from this point to the position transducer core 31, whereby it may be precisely predetermined and remain constant. The effects of any lateral displacements on measurement accuracy are minimized by means of precision machining of the flat sheet-contacting surface on the contact shoe 25 and reference surface 26. Further, positioning linear variable differential transformer 22 substantially within pneumatic chamber 24 and arranging for a constant air flow through the chamber, serves to increase thermal stability, thereby minimizing the adverse effects of temperature variation on measurement accuracy.

Although the invention has been described in terms of the preferred embodiment, it is apparent that numerous equivalents may be resorted to without departing from the essence of the invention as defined by the following claims.

I claim:

1. An improved basis weight measuring device comprising:
    a basis weight gauge including a radiation source and a radiation sensor, said source and said sensor being disposed at opposite sides of a gap through which passes a sheet of material to be measured, said sensor providing signals indicative of the basis weight of the sheet; and
    means for continuously measuring said gap and adjusting said sensor signals in response thereto; the improvement wherein said gap measuring means comprises:
    caliper means for measuring the thickness of said sheet of material, said caliper means including a first portion riding on said sheet as it passes through said gap and urging said sheet against a first side of said gap; and
    first portion sensing means for measuring the distance between a reference point on said first portion of said caliper means and the second side of said gap.

2. The improved basis weight measuring device of claim 1, wherein said first portion sensing means comprises a two element electromagnetic sensing device, one element of which is connected to said first portion of said caliper means and the other element of which is disposed on said second side of said gap.

3. The improved basis weight measuring device of claim 1, wherein said caliper means comprises a two element electromagnetic sensing device, one element of which is disposed in said first portion of said caliper means and the other element of which is disposed on said first side of said gap.

* * * * *